United States Patent
Imai (10) Patent No.: US 11,960,649 B2
(45) Date of Patent: Apr. 16, 2024

(54) ELECTRONIC APPARATUS CONFIGURED TO DETERMINE A CURRENT WORN POSITION AMONG PLURAL WEARABLE POSITIONS, AND STORAGE MEDIUM

(71) Applicant: CASIO COMPUTER CO., LTD., Tokyo (JP)

(72) Inventor: Yuji Imai, Akishima (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 0 days.

(21) Appl. No.: 18/027,148

(22) PCT Filed: Aug. 31, 2021

(86) PCT No.: PCT/JP2021/031970
§ 371 (c)(1),
(2) Date: Mar. 20, 2023

(87) PCT Pub. No.: WO2022/064978
PCT Pub. Date: Mar. 31, 2022

(65) Prior Publication Data
US 2023/0333654 A1    Oct. 19, 2023

(30) Foreign Application Priority Data

Sep. 24, 2020    (JP) ................................. 2020-159193

(51) Int. Cl.
*G06F 3/01*    (2006.01)
*A61B 5/00*    (2006.01)
(Continued)

(52) U.S. Cl.
CPC .......... *G06F 3/015* (2013.01); *A61B 5/02438* (2013.01); *A61B 5/681* (2013.01); *G04G 21/025* (2013.01); *A61B 2562/043* (2013.01)

(58) Field of Classification Search
CPC ..... G06F 3/015; A61B 5/02438; A61B 5/681; A61B 2562/043; G04G 21/025
See application file for complete search history.

(56) References Cited

U.S. PATENT DOCUMENTS

| 10,765,365 B2 * | 9/2020 | Liu ..................... A44C 5/0023 |
| 2015/0022438 A1 | 1/2015 | Hong |
| 2020/0345245 A1 | 11/2020 | Mori et al. |

FOREIGN PATENT DOCUMENTS

| CN | 106371816 A | 2/2017 |
| JP | S62155391 U | 10/1987 |

(Continued)

OTHER PUBLICATIONS

Machine Translation of CN106371816B (Year: 2017).*
(Continued)

*Primary Examiner* — Rodney Amadiz
(74) *Attorney, Agent, or Firm* — Holtz, Holtz & Volek PC (57) ABSTRACT

An electronic apparatus to be worn on a wrist of a user includes a first pulse sensor, a second pulse sensor, and a processor. The second pulse sensor is provided at a different position from the first pulse sensor in a direction from an arm to a fingertip when the user wears the electronic apparatus. The processor determines whether the electronic apparatus is worn on a right wrist or on a left wrist based on a difference between a timing at which the first pulse sensor detects a predetermined pulse and a timing at which the second pulse sensor detects the pulse.

11 Claims, 6 Drawing Sheets

(51) Int. Cl.
    *A61B 5/024*      (2006.01)
    *G04G 21/02*      (2010.01)

(56)          References Cited

FOREIGN PATENT DOCUMENTS

JP         2002148375  A       5/2002
JP         2013061176  A       4/2013
JP         2019110987  A       7/2019
JP         2020085736  A       6/2020

OTHER PUBLICATIONS

Machine Translation of JP2013061176A (Year: 2013).*
International Search Report (ISR) (and English language translation thereof) dated Nov. 30, 2021, issued in International Application No. PCT/JP2021/031970.
Written Opinion dated Nov. 30, 2021, issued in International Application No. PCT/JP2021/031970.
International Preliminary Report on Patentability (IPRP) (and an English language translation thereof) dated Mar. 28, 2023, issued in International Application No. PCT/JP2021/031970.

* cited by examiner

ELECTRONIC APPARATUS CONFIGURED TO DETERMINE A CURRENT WORN POSITION AMONG PLURAL WEARABLE POSITIONS, AND STORAGE MEDIUM

TECHNICAL FIELD

The present invention relates to an electronic apparatus and a storage medium.

BACKGROUND ART

Conventionally, many devices worn on the wrist, such as wristwatches and wearable devices, have been designed to be operated on the left wrist, since many people are right-handed. Therefore, there was a problem that devices designed to be worn on the left wrist were difficult to be operated when worn on the right wrist.

One way to solve the above problem involves operating buttons or menus for switching between a right wrist mode and a left wrist mode.

In this regard, according to the technology described in Patent Document 1, a user chooses between a right wrist wearing mode and a left wrist wearing mode to switch. functions assigned to respective buttons.

According to the technology described in Patent Document 2, a user chooses between a right wrist wearing mode and a left wrist wearing mode to reverse the left and right sides of the screen.

CITATION LIST

Patent Literature
Patent Document 1: JP S62-155391 U
Patent Document 2: JP 2002-148375 A

SUMMARY OF INVENTION

Technical Problem

Such methods in which a user operates buttons or menus to switch between the right wrist mode and the left wrist mode has problems that the operation is cumbersome and is easily forgotten, or that the menu operations are too complicated to remember.

The method of automatically determining whether the device is worn on the right wrist or on the left wrist based on an angle using an angle sensor mounted on the device has a problem that the determination is difficult because the hands are continually moving. The method of automatically determining whether the device is worn on the right wrist or on the left wrist based on face recognition using a camera mounted on the device has a problem that the determination cannot be made unless the camera captures the face.

The purpose of the present invention is to provide an electronic apparatus and a storage medium that enables easy determination of whether the device is worn on the right wrist or on the left wrist.

Solution to Problem

In order to solve the above problem, an electronic apparatus of one aspect of the present invention is an electronic apparatus configured to be worn on a wrist of a user including:
a first pulse sensor;
a second pulse sensor that is arranged to be provided at a different position from the first pulse sensor in a direction from an arm to a fingertip in a case in which the user wears the electronic apparatus; and
a processor that determines whether the electronic apparatus is worn on a right wrist or on a left wrist based on a difference between a timing at which the first pulse sensor detects a predetermined pulse and a timing at which the second pulse sensor detects the pulse.

Advantageous Effects of Invention

According to the present invention, it possible to easily deter mine whether the device is worn on the right wrist or on the left wrist.

DESCRIPTION OF EMBODIMENTS

In the following, embodiments of the present invention are described with reference to the drawings. However, the scope of the present invention is not limited to the following embodiments and the drawings.

<Configuration of Electronic Apparatus>

First, an overview of an electronic apparatus 100 as an electronic apparatus of the present embodiment will be described.

Figure 1:
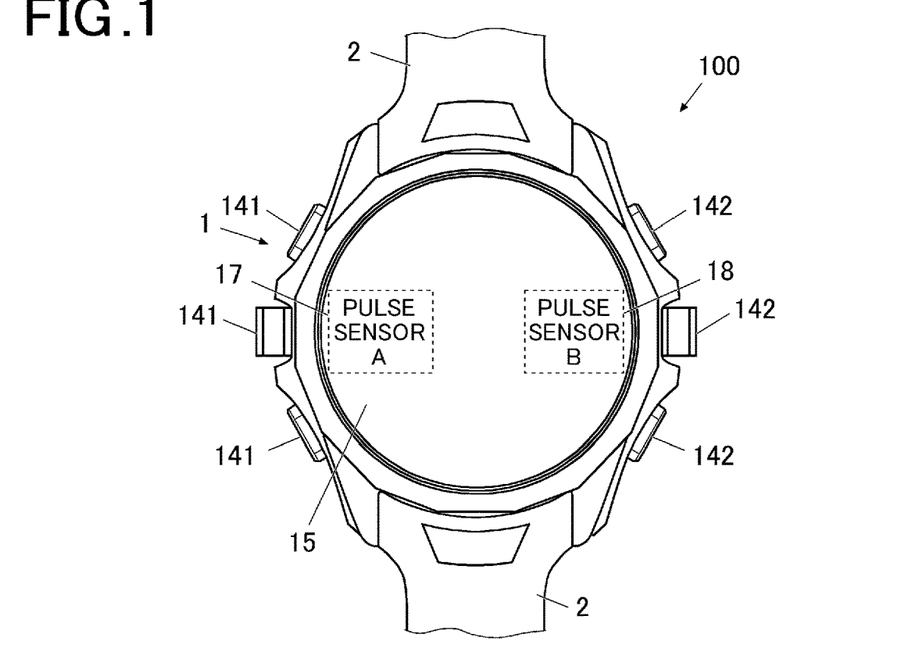
FIG. 1 This is an external view of a front surface of an electronic apparatus, showing positions of pulse sensors.

FIG. 1 is an external view of a front surface of the electronic apparatus 100 of the present invention, showing positions of a pulse sensor A17 and a pulse sensor B18.

As illustrated in. FIG. 1, the electronic apparatus 100 is in the form of a wristwatch and has a main body 1 and a band 2.

The main body 1 has a display 15 (described later) on its upper surface. The main body 1 has an operation button(s) 141 on its left side and an operation button(s) 142 on its right side. In the present embodiment, the number of operation buttons 141 and the number of operation buttons 142 are each three, but are not limited to this number, as long as one or more operation buttons 141 and one or more operation buttons 142 are provided. When the band 2, described later, extends in the direction of the 12 o'clock position in an analog watch, the pulse sensor A17 is provided at a position biased toward the 9 o'clock position in the main body 1, and the pulse sensor B18 is provided at a position biased toward the 3 o'clock position. in the main body 1. That is, the pulse rate sensor A17 and the pulse rate sensor B18 are positioned so as to be separated from each other in a direction from an arm to a fingertip when the electronic apparatus 100 is worn on a wrist of the user. The pulse sensor A17 is provided so as to be positioned more biased toward the arm in the direction from the arm to the fingertip than the pulse sensor B18 when the electronic apparatus 100 is worn on a left wrist of the user.

The band 2 fastens the main body 1 to the wrist of the user.

Next, the functional configuration of the electronic apparatus 100 is described with reference to FIG. 2.

Figure 2:
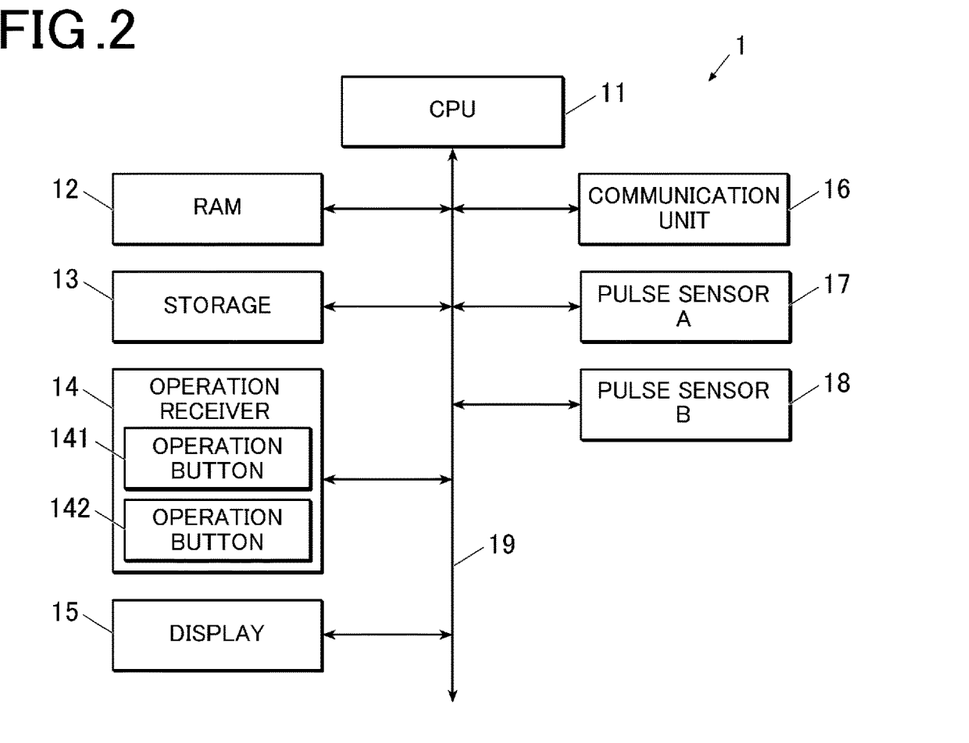
FIG. 2 This is a block diagram illustrating an overall configuration of the electronic apparatus.

FIG. 2 is a block diagram illustrating the functional configuration of the electronic apparatus 100.

As illustrated in FIG. 2, the main body 1 of the electronic apparatus 100 includes a CPU (Central Processing Unit) 11, a RAM (Random Access Memory) 12, a storage 13, an operation receiver 14, a display 15, a communication unit 16, a pulse sensor A17, a pulse sensor B18, and the like, and each unit is connected through a bus 19.

The CPU 11 is a processor that controls each unit of the main body 1. The CPU 11 reads out a program stored in the storage 13, develops the program in the RAM 12, and executes the program to perform various arithmetic processes.

The CPU 11 also determines whether the electronic apparatus 100 is worn on the right wrist or on the left wrist based on a difference between the timing at which the first pulse sensor (pulse sensor A17) detects a predetermined pulse and the timing at which the second pulse sensor (pulse sensor B18) detects the pulse. Here, the CPU 11 functions as a determiner.

The CPU 11 switches functions assigned to the operation buttons 141 and the operation button 142 according to the determination result by the determiner. Here, the CPU 11 functions as a switch controller.

The CPU 11 changes order of the menus displayed on the display 15, or changes orientation of a screen displayed on the display 15 according to the determination result by the determiner. Here, the CPU 11 functions as a display controller.

The 12 provides the CPU 11 with a memory space for work and stores temporary data. The RAM 12 may include a nonvolatile memory.

The storage 13 stores various kinds of data such as a program (including a determination process described later) executed by the CPU 11 and setting data. The program is stored in the storage 13 in a form of a computer readable program code. Examples of the storage 13 include a flash memory, which is a storage device that does not need a power supply in order to maintain data.

The operation receiver 14 includes the operation buttons 141 on the left side of the main body 1, the operation buttons 142 on the right side of the main body 1, and a touch sensor on the display 15, which is not shown in the drawing. The operation receiver 14 receives input operation by the user, converts the contents of the operation to electrical signals, and outputs the signals to the CPU 11.

The display 15 includes a LCD (Liquid Crystal Display) and displays a screen according to display control signals from the CPU 11. The above touch sensor is provided on the screen displayed on the display 15, and functions as a touch panel type operating/displaying means.

The communication unit 16 is a communication module including an antenna, a modulating/demodulating circuit, a signal processing circuit, and the like. For example, the communication unit 16 performs wireless data communication with an external terminal apparatus according to a communication standard related to short range wireless communication with BLE (Bluetooth (registered trademark) Low Energy).

Figure 3:
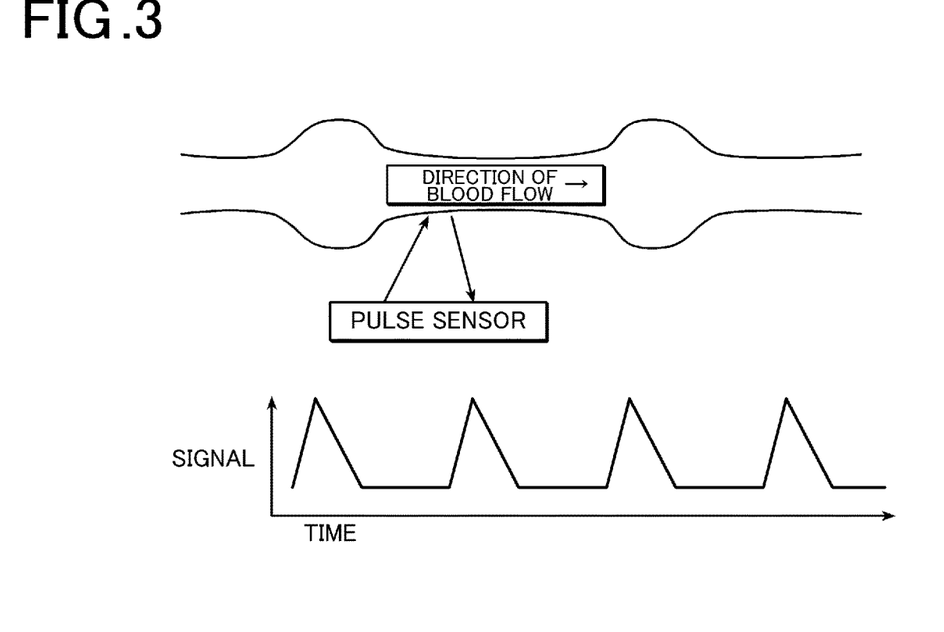
FIG. 3 This is a diagram illustrating a principle of the pulse sensor.

The pulse sensor A17 and the pulse sensor B18 each have a light-receiving element and a light-emitting element. FIG. 3 illustrates the principle of the pulse sensor. The light-emitting element is a light emitting diode that emits green light, for example, light with a wavelength of 520 nm to 530 nm, which is well absorbed by hemoglobin in the blood within the area where the light-emitting element emits the light. The light-receiving element receives reflection of the light emitted to the wrist by the light-emitting element and outputs an electric signal of an electric amount corresponding to intensity of the received light.

The state of pulse can be measured in time series as the pulse sensor A17 and the pulse sensor B18 measure changes in light absorption, that is, changes in the capacity of arterial blood vessels, the blood flow that changes with the heartbeat. An example of the measurement result is illustrated at the bottom of FIG. 3.

The pulse sensor A17 and the pulse sensor B18 output the measurement result to the CPU 11.

Figure 4:
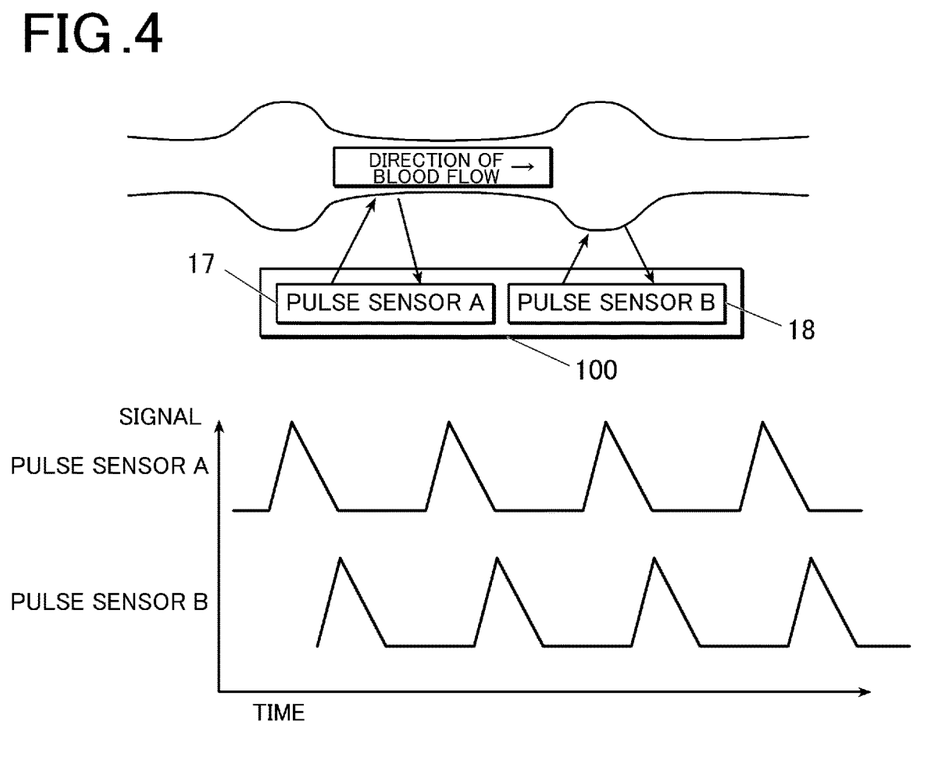
FIG. 4 This is a diagram illustrating an example of pulse detection with two pulse sensors.

FIG. 4 illustrates an example of pulse detection with the pulse sensor A17 and the pulse sensor B18. When the blood flows from left to right, that as, from the pulse sensor A17 side to the pulse sensor B18 side, pulse waveforms that are almost analogous to each other and with a predetermined time difference, can be measured as illustrated in the bottom of FIG. 4.

Figure 5:
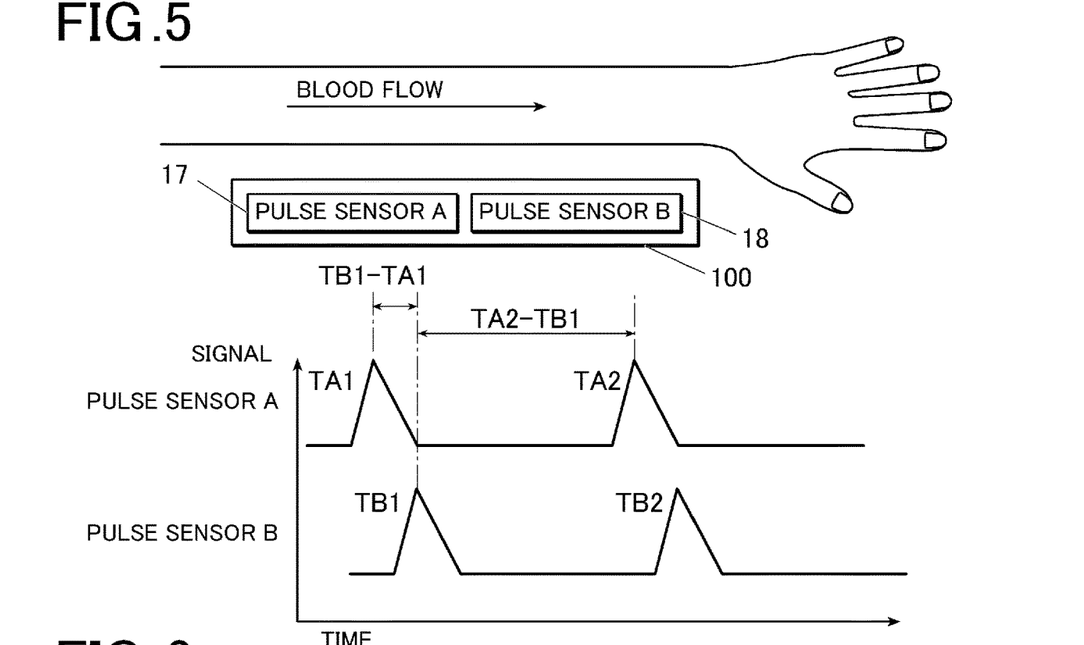
FIG. 5 This is a diagram illustrating as example of pulse detection with two pulse sensors when the electronic apparatus is worn on a left wrist.

FIG. 5 illustrates an example of detection by the pulse sensor A17 and the pulse sensor B18 when the electronic apparatus 100 is worn on the left wrist. When the electronic apparatus 100 is worn on the left wrist, the blood flows from left to right, that is, from the pulse sensor A17 side to the pulse sensor B18 side. Since the pulse sensor A17 is at the upstream side of the blood flow, the pulse sensor A17 detects the change in pulse first, and the pulse sensor B18 detects the change in pulse a little later. The peak time of the first pulse detected by the pulse sensor A17 is TA1, the peak time of the second pulse is TA2, and the peak time of the first pulse detected by the pulse sensor B18 after TA1 is TB1. Then, waveforms shown in the bottom of FIG. 5 are obtained, and TA1, TA2, and TB1 satisfy the following inequality (1). That is, when a first time period (TB1-TA1) from the detection of the first pulse by the pulse sensor A17 to the detection of the first pulse by the pulse sensor B18 is shorter than a second time period (TA2-TB1) from the detection of the first pulse by the pulse sensor B18 to the detection of the second pulse by the pulse sensor A17, the CPU 11 determines that the electronic apparatus 100 is worn on the left wrist.

$$TB1-TA1<TA2-TB1 \qquad (1)$$

Figure 6:
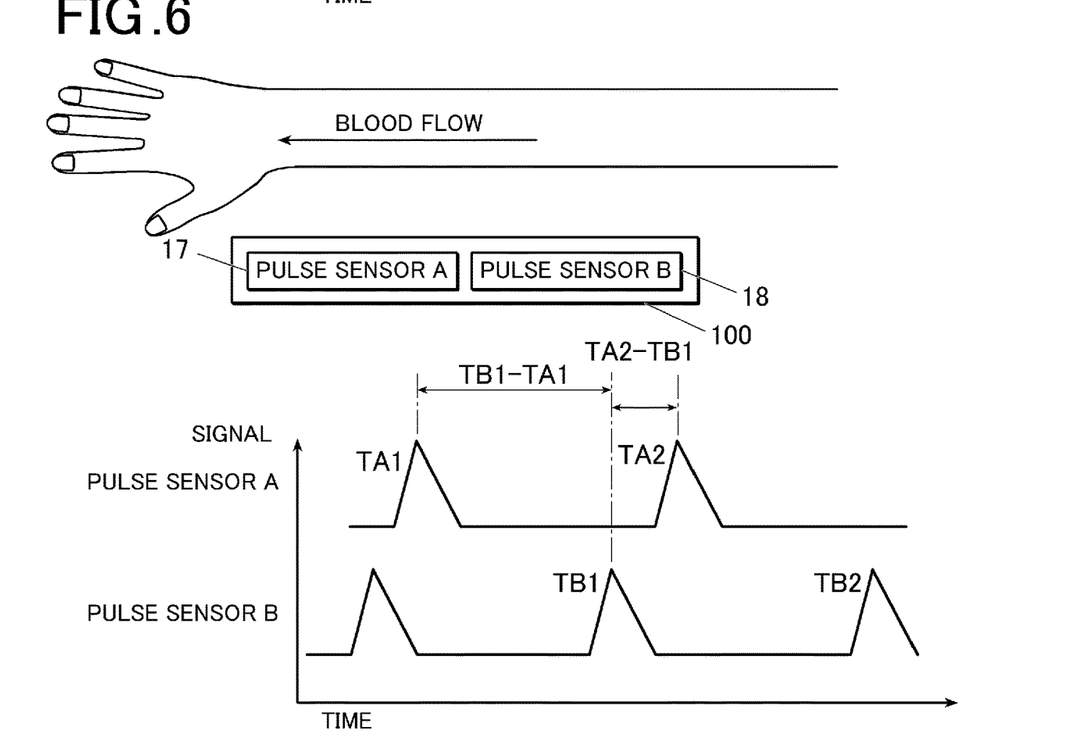
FIG. 6 This is a diagram illustrating an example of pulse detection with two pulse sensors when the electronic apparatus is worn on a right wrist.

FIG. 6 illustrates an example of detection by the pulse sensor A17 and the pulse sensor B18 when the electronic apparatus 100 is worn on the right wrist. When the electronic apparatus 100 is worn on the right wrist, the blood flows from right to left, that is, from the pulse sensor A18 side to the pulse sensor B17 side. Since the pulse sensor A18 is at the upstream side of the blood flow, the pulse sensor A18 detects the change in pulse first, and the pulse sensor B17 detects the change in pulse a little later. The peak time of the first pulse detected by the pulse sensor A17 is TA1, the peak time of the second pulse is TA2, and the peak time of the first pulse detected by the pulse sensor B18 after TA1 is TB1. Then, waveforms shown in the bottom of FIG. 6 are obtained, and TA1, TA2, and TB1 satisfy the following inequality (2). That is, when the first time period (TB1-TA1)

from the detection of the first pulse by the pulse sensor A17 to the detection of the first pulse by the pulse sensor B18 is longer than the second time period (TA2-TB1) from the detection of the first pulse by the pulse sensor B18 to the detection of the second pulse by the pulse sensor A17, the CPU 11 determines that the electronic apparatus 100 is worn on the right wrist.

$$TB1-TA1>TA2-TB1 \quad (2)$$

<Overview of Operation of Electronic Apparatus>

Next, the operation of the electronic apparatus 100 of the present embodiment is described.

Figure 7:
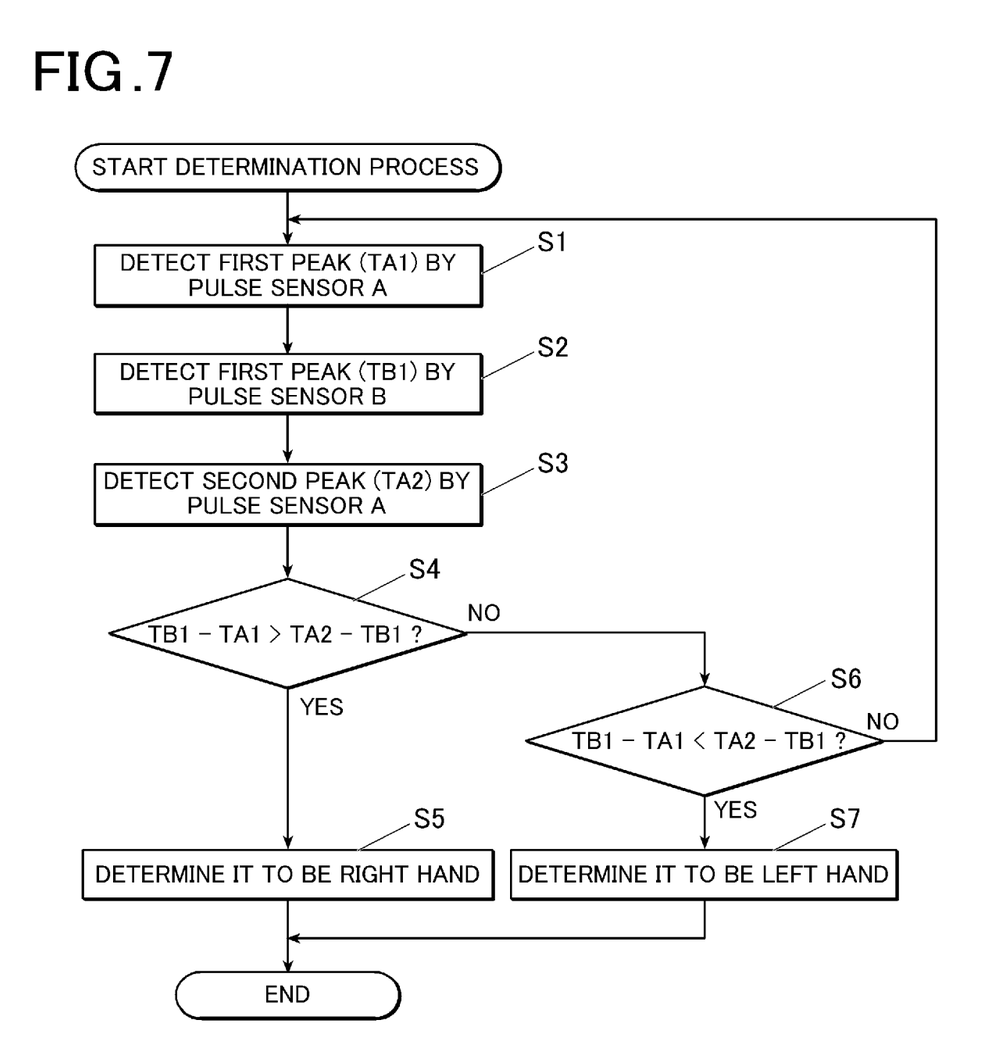
FIG. 7 This is a flowchart showing steps in a determination process performed by the electronic apparatus.

The CPU 11 starts the determination process illustrated in FIG. 7 in the case that the user wears the electronic apparatus 100 on his/her arm. The determination process is executed by a program stored in the storage 13.

The CPU 11 may sense that the electronic device 100 is worn on the arm using a sensor provided for that purpose, or upon the user pressing a predetermined button after wearing the electronic apparatus 100 on the wrist.

First, the CPU 11 controls the pulse sensor A17 to detect TA1, which is the peak time of the first pulse (Step S1).

Next, the CPU 11 controls the pulse sensor A18 to detect TB1, which is the peak time of the first pulse (Step S2).

Next, the CPU 11 controls the pulse sensor A17 to detect TA2, which is the peak time of the second pulse (Step S3).

Next, the CPU 11 compares "TB1-TA1" and "TA2-TB1" using TA1, TA2, and TB1 obtained in Steps S1 to S3 and determines whether or not "TB1-TA1>TA2-TB1" is satisfied (Step S4).

If "TB1-TA1>TA2-TB1" is satisfied, (Step S4: YES), the CPU 11 determines that the electronic apparatus 100 is worn on the right wrist (Step S5) and finishes the process.

If "TB1-TA1>TA2-TB1" is not satisfied (Step S4; NO), the CPU 11 determines whether or not "TB1-TA1<TA2-TB1" (Step S6). If "TB1-TA1<TA2-TB1" is satisfied (Step S6: YES), the CPU 11 determines that the electronic apparatus 100 is wore on the left wrist (Step S7) and finishes the process.

If "TB1-TA1<TA2-TB1" is not satisfied (Step S6; NO), the CPU 11 returns the process to Step S1.

When the CPU 11 has determined whether the electronic apparatus 100 is worn on the right wrist or on left wrist through the determination process, the CPU 11 switches the functions of the operation buttons 141, 142 and the order of the menus displayed on the display 15 according to the determination result.

Frequently used functions of the electronic apparatus 100 (for example, start/stop functions of a stopwatch) are more easily operated when assigned to the operation buttons closer to the fingertips. Therefore, when the electronic apparatus 100 is worn on the left wrist, the CPU 11 assigns the most frequently used functions to the operation buttons 142 that are close to the fingertip. The CPU 11 accordingly displays the frequently used menu on the right side of the display 15, the operation button 142 side. Further, when the electronic apparatus 100 is worn on the right wrist, the CPU 11 assigns the most frequently used functions to the operation buttons 141 that are close to the fingertip. The CPU 11 accordingly displays the frequently used menu on the left side of the display 15, the operation button 141 side.

Figure 8:
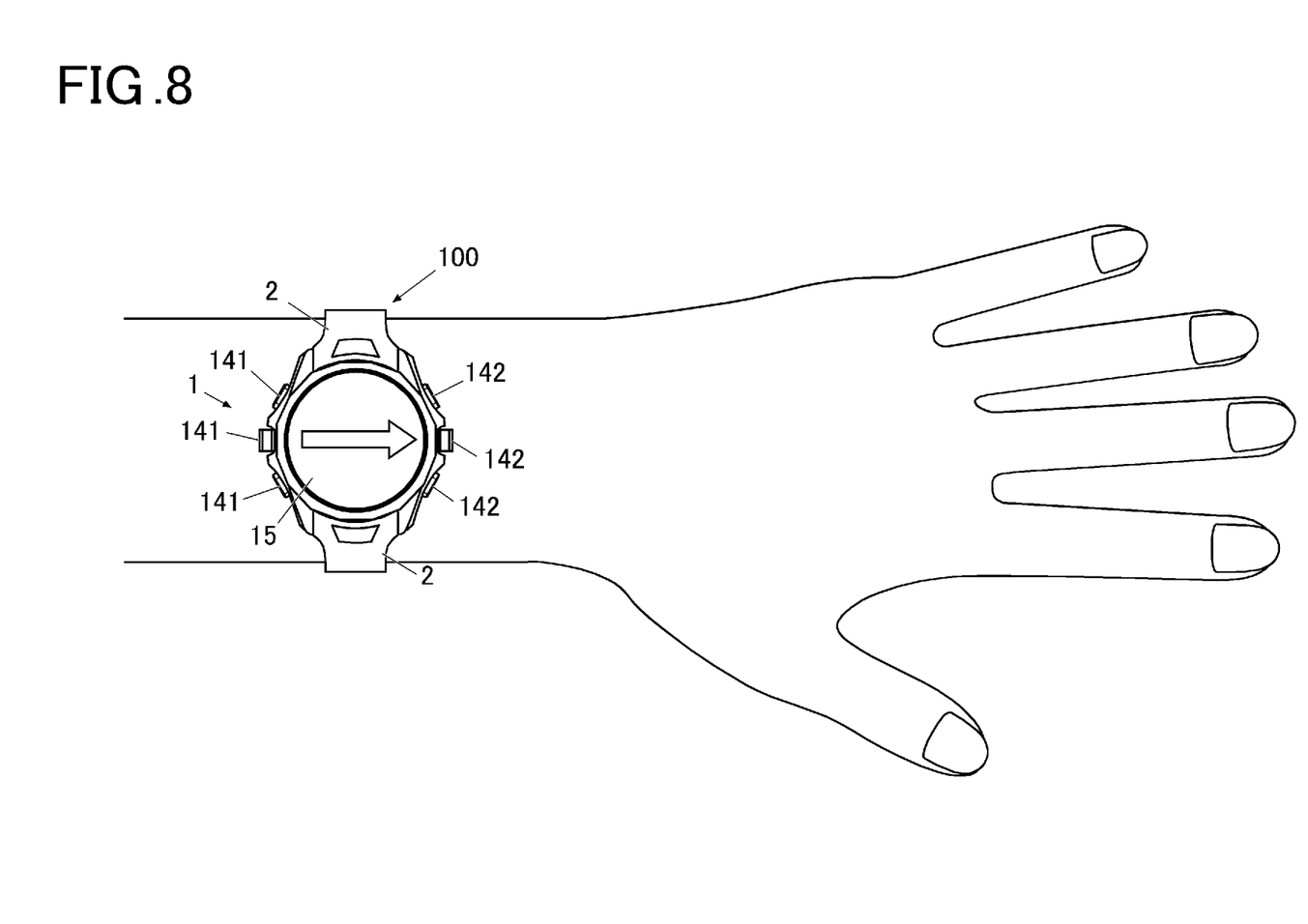
FIG. 8 This is a diagram illustrating as example of a vertical writing display when the electronic apparatus is worn on a left wrist.
Figure 9:
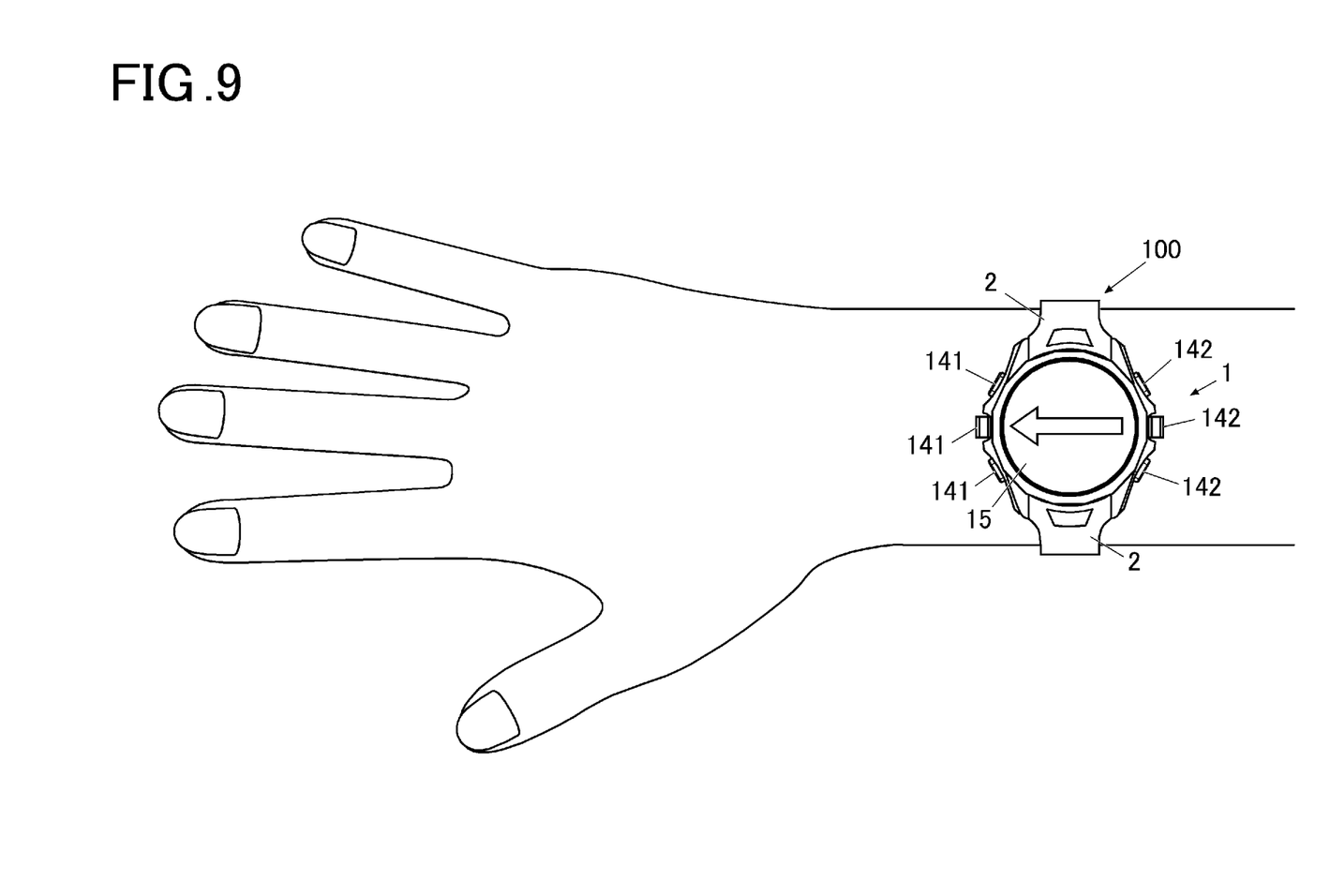
FIG. 9 This is a diagram illustrating an example of a vertical writing display when the electronic apparatus is worn on a right wrist.

When a left-to-right or right-to left vertical writing display (for example, vertically written sentences) is made on the display 15 shown in FIG. 8 and FIG. 9, the CPU 11 switches the direction of the vertical writing display according to the determination result of the determination process.

When the electronic apparatus 100 is worn on the left wrist as illustrated in FIG. 8, the CPU 11 displays the vertical writing display from left to right on the display 15. When the electronic apparatus 100 is worn on the right wrist as illustrated in FIG. 9, the CPU 11 displays the vertical writing display from right to left on the display 15. The arrows in FIG. 8 and FIG. 9 indicate the direction of the display.

The electronic apparatus 100 of the above embodiments is an electronic apparatus 100 worn on the wrist of the user, and includes the first pulse sensor (pulse sensor A17), the second pulse sensor (pulse sensor B18) provided at a different position from the first pulse sensor in the direction from the arm to the fingertip in the case that the user wears the electronic apparatus 100, and the determiner (CPU 11) that determines whether the electronic apparatus is worn on the right wrist or on the left wrist based on the difference between the timing at which the first pulse sensor detects a predetermined pulse and the timing at which the second pulse sensor detects the pulse.

Thus, it is possible to easily determine whether the device is worn on the right wrist or on the left wrist.

The determiner (CPU 11) also determines whether the electronic apparatus 100 is worn on the right wrist or on left wrist based on the first time period from the detection of the first pulse by the first pulse sensor (pulse sensor A17) to the detection of the first pulse by the second pulse sensor (pulse sensor B18) and the second time period from the detection of the first pulse by the second pulse sensor to the detection of the second pulse by the first pulse sensor.

Thus, it is possible to easily determine whether the device is worn on the right wrist or on the left wrist based on the first time period and the second time period.

When the electronic apparatus 100 is worn on the left wrist, the first pulse sensor (pulse sensor A17) is provided so as to be positioned more biased toward the arm in the direction from the arm to the fingertip than the second pulse sensor (pulse sensor B18). The determiner (CPU 11) determines that the electronic apparatus 100 is worn on the left wrist when the first time period is shorter than the second time period, and that the electronic apparatus 100 is worn on the right wrist when the first time period is longer than the second time period.

Thus, it is possible to easily determine whether the device is worn on the right wrist or on the left wrist based on the difference between the first time period and the second time period.

The electronic apparatus 100 has the determiner (CPU 11) that switches the function(s) assigned to the operation receiver (operation buttons 141, 142) according to the determination result by the determiner (CPU 11).

Thus, it is possible to realize a user-friendly electronic apparatus 100 according to the determination result by the determiner.

The electronic apparatus 100 has the display controller (CPU 11) that changes the order of the menus displayed on the display 15 according to the determination result by the determiner (CPU 11).

Thus, it is possible to realize a user-friendly electronic apparatus 100 according to the determination result by the determiner.

The electronic apparatus 100 has the display controller (CPU 11) that changes the orientation of the screen displayed on the display 15 according to the determination result by the determiner (CPU 11).

Thus, it is possible to realize a user-friendly electronic apparatus 100 according to the determination result by the determiner.

It goes without saying that the present invention is not limited to the above embodiments, etc., and can be modified as appropriate without departing from the scope of the present invention.

For example, in the above embodiment, the pulse sensor A17 is provided at the 9 o'clock position of the main body 1, and the pulse sensor B18 is provided at the 3 o'clock position of the main body 1, but the present invention is not limited to this embodiment. The interval between the pulse sensor A17 and the pulse sensor B18 only needs to be long enough to detect differences in the peak of the pulse waveform.

The pulse sensors A17 and B18 are each provided with a light-receiving element and a light-emitting element in the above embodiment, but the present invention is not limited to this embodiment. Only one of the pulse sensors may be provided with a light-emitting element, such that two light-receiving elements receive reflection of light from the one light-emitting element.

In the above embodiment, the CPU 11 displays the vertical writing display from left to right on the display 15 when the electronic apparatus 100 is worn on the left wrist, and from right to left on the display 15 when the electronic apparatus 100 is worn on the right wrist, but the present invention is not limited to this embodiment. The CPU 11 may display the vertical writing display from right to left on the display 15 when the electronic apparatus 100 is worn on the left wrist, and from left to right on the display 15 when the electronic apparatus 100 is worn on the right wrist.

When the electronic apparatus 100 of the above embodiment is applied to a blood pressure monitor, information on which wrist the blood pressure was measured can be automatically recorded based on the determination result of whether the electronic apparatus 100 is worn on the right wrist or on the left wrist.

Embodiments of the present invention have been described. However, the scope of the present invention is not limited to the above embodiments, and the scope of the present invention includes the scope as claimed and its equivalents.

This application is based on Japanese Patent Application No. 2020-159193 filed on Sep. 24, 2020. The specification, claims, and drawings of Japanese Patent Application No. 2020-159193 are incorporated herein by reference is its entirety.

INDUSTRIAL APPLICABILITY

The present invention can be applied to an electronic apparatus and a program to control the electronic apparatus.

REFERENCE SIGNS LIST 100 electronic apparatus
1 main body
2 band
11 CPU (determiner, switch controller, display controller)
12 RAM
13 storage
14 operation receiver
141 operation button
142 operation button
15 display
16 communication unit
17 pulse sensor A17
18 pulse sensor B18
19 bus

The invention claimed is:

1. An electronic apparatus configured to be worn on a wrist of a user, the electronic apparatus comprising:
   a first pulse sensor;
   a second pulse sensor that is arranged to be provided at a different position from the first pulse sensor in a direction from an arm to a fingertip in a case in which the user wears the electronic apparatus; and
   a processor that determines whether the electronic apparatus is worn on a right wrist or on a left wrist based on a comparison between (i) a first time period from detection of a first pulse by the first pulse sensor to detection of the first pulse by the second pulse sensor, and (ii) a second time period from detection of the first pulse by the second pulse sensor to detection of a second pulse by the first pulse sensor.

2. The electronic apparatus according to claim 1, wherein in a case in which the electronic apparatus is worn on the left wrist, the first pulse sensor is provided so as to be positioned more toward the arm in the direction from the arm to the fingertip than the second pulse sensor,
   wherein, upon the first time period being shorter than the second time period, the processor determines that the electronic apparatus is worn on the left wrist, and
   wherein, upon the first time period being longer than the second time period, the processor determines that the electronic apparatus is worn on the right wrist.

3. The electronic apparatus according to claim 2, wherein the processor switches a function assigned to an operation receiver based on a determination result of whether the electronic apparatus is worn on the right wrist or on the left wrist and frequencies of use of respective functions of the electronic apparatus.

4. The electronic apparatus according to claim 2, wherein the processor changes an arrangement of a menu that is displayed on a display in response to a determination result of whether the electronic apparatus is worn on the right wrist or on the left wrist.

5. The electronic apparatus according to claim 2, wherein the processor changes an orientation of a screen displayed on a display in response to a determination result of whether the electronic apparatus is worn on the right wrist or on the left wrist.

6. The electronic apparatus according to claim 1, wherein the processor switches a function assigned to an operation receiver based on a determination result of whether the electronic apparatus is worn on the right wrist or on the left wrist and frequencies of use of respective functions of the electronic apparatus.

7. The electronic apparatus according to claim 6, wherein the processor changes an arrangement of a menu that is displayed on a display in response to the determination result.

8. The electronic apparatus according to claim 6, wherein the processor changes an orientation of a screen displayed on a display in response to the determination result.

9. The electronic apparatus according to claim 1, wherein the processor changes an order of a menu that is displayed on a display in response to a determination result of whether the electronic apparatus is worn on the right wrist or on the left wrist.

10. The electronic apparatus according to claim 1, wherein the processor changes an orientation of a screen displayed on a display in response to a determination result of whether the electronic apparatus is worn on the right wrist or on the left wrist.

11. A non-transitory computer-readable storage medium storing a program that is executable by a computer of an electronic apparatus that is configured to be worn on a wrist of a user and includes a first pulse sensor and a second pulse sensor that is arranged to be provided at a different position from the first pulse sensor in a direction from an arm to a fingertip in a case in which the user wears the electronic apparatus, the program being executable by the computer to control the electronic apparatus to perform operations comprising:

determining whether the electronic apparatus is worn on a right wrist or on a left wrist based on a comparison between (i) a first time period from detection of a first pulse by the first pulse sensor to detection of the first pulse by the second pulse sensor, and (ii) a second time period from detection of the first pulse by the second pulse sensor to detection of a second pulse by the first pulse sensor.

\* \* \* \* \*